(12) United States Patent
Giudiceandrea

(10) Patent No.: US 8,413,522 B2
(45) Date of Patent: Apr. 9, 2013

(54) DEVICE AND METHOD FOR PROOF LOADING WOODEN BOARDS

(75) Inventor: Federico Giudiceandrea, Bressanone (IT)

(73) Assignee: Microtec S.R.L., Bressanone (IT)

( * ) Notice: Subject to any disclaimer, the term of this patent is extended or adjusted under 35 U.S.C. 154(b) by 0 days.

(21) Appl. No.: 12/988,601

(22) PCT Filed: Sep. 24, 2008

(86) PCT No.: PCT/IB2008/053884
§ 371 (c)(1),
(2), (4) Date: Oct. 25, 2010

(87) PCT Pub. No.: WO2010/035066
PCT Pub. Date: Apr. 1, 2010

(65) Prior Publication Data
US 2011/0030481 A1 Feb. 10, 2011

(51) Int. Cl.
*G01N 3/08* (2006.01)
(52) U.S. Cl. .......................................................... 73/831
(58) Field of Classification Search .................... 73/831, 73/826, 849
See application file for complete search history.

(56) References Cited

U.S. PATENT DOCUMENTS

| | | | |
|---|---|---|---|
| 3,714,820 A | 2/1973 | Strickler et al. | |
| 4,627,293 A | 12/1986 | Bechtel | |
| 5,024,091 A | 6/1991 | Pellerin et al. | |
| 5,503,024 A * | 4/1996 | Bechtel et al. | 73/852 |
| 5,679,191 A * | 10/1997 | Robinson | 156/64 |
| 7,975,830 B2 * | 7/2011 | Bacher et al. | 198/461.2 |
| 8,250,922 B2 * | 8/2012 | Giudiceandrea | 73/597 |
| 8,262,074 B2 * | 9/2012 | Langenegger | 270/52.22 |
| 2006/0259252 A1 | 11/2006 | Leitinger et al. | |
| 2012/0099167 A1 * | 4/2012 | Ciardullo | 358/498 |

FOREIGN PATENT DOCUMENTS

DE 4435975 A1 4/1995

\* cited by examiner

*Primary Examiner* — Max Noori
(74) *Attorney, Agent, or Firm* — Pearne & Gordon LLP

(57) ABSTRACT

A device for proof loading wooden boards including a deformer (9) for deforming the boards (2) which is designed to cause the boards (2) to elongate along their main direction of extension, said deformer including first and second feeders (3), (4) positioned at a first and a second segment (5), (6) of a feed path along which the boards (2) are fed parallel with their main direction of extension, and being able to apply a longitudinal tractive force on the boards (2) using the first and the second feeders (3), (4). A method for proof loading wooden boards is also disclosed, which can be implemented without interrupting board feed along its feed path.

20 Claims, 3 Drawing Sheets

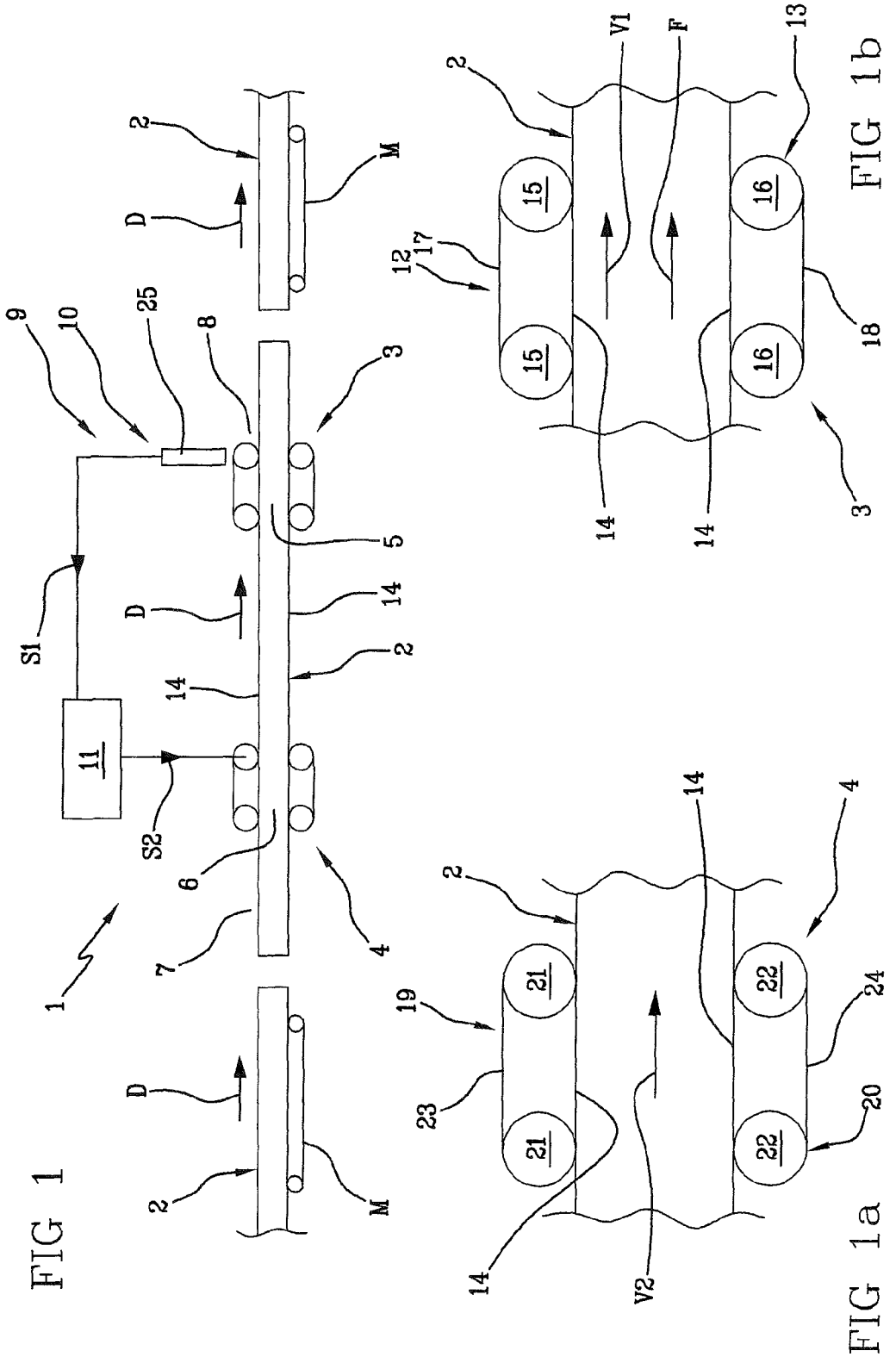

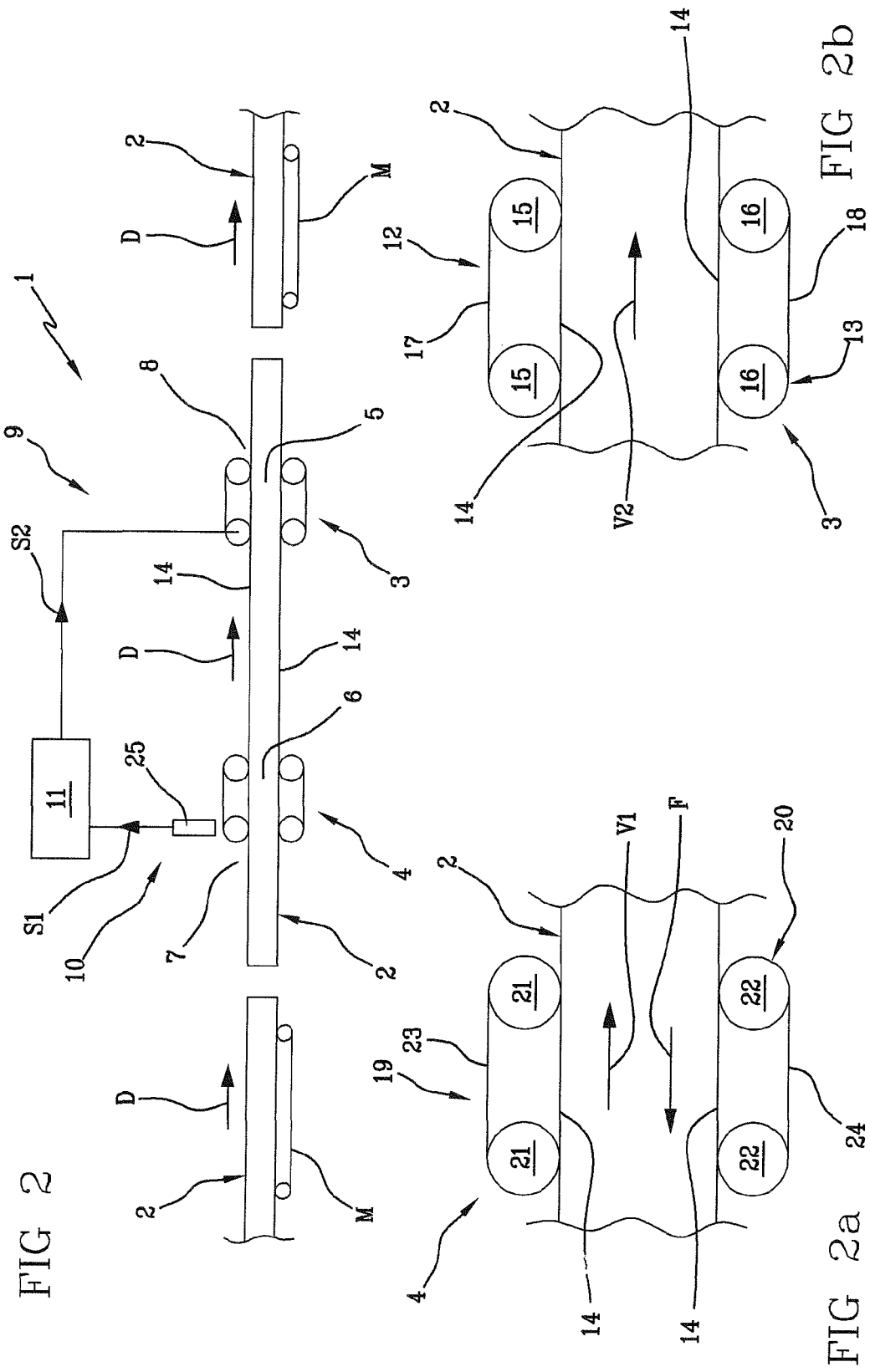

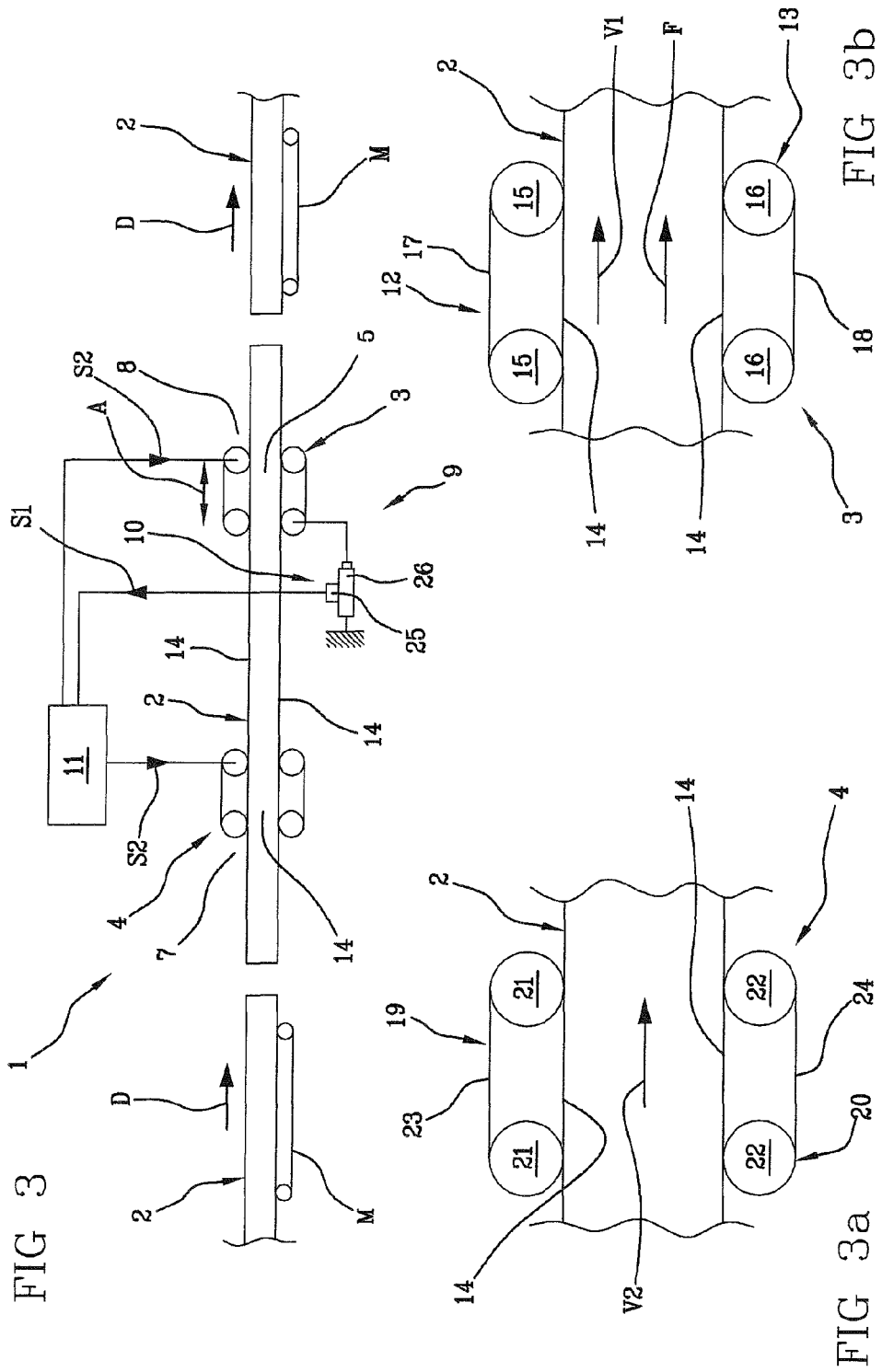

DEVICE AND METHOD FOR PROOF LOADING WOODEN BOARDS

The present invention relates to a device and a method for proof loading wooden boards. The term proof loading, commonly used in the sector, is used to mean the execution of a tensile test on the boards which may aim only to test the resistance of the boards to a predetermined load, or may also allow calculation of the modulus of elasticity of the boards.

In particular, said invention is advantageously applied in sawmills, in timber industries or the like, to evaluate mechanical properties of wooden boards.

Therefore, the present invention has for an aim both proof loading for testing wooden boards, and for allowing the calculation of their modulus of elasticity.

The modulus of elasticity, normally labelled E, consists of the ratio of the value of a tensile force applied to a material (which must be less than the breaking load or elastic failure set load for the material), to the elastic deformation induced by said force.

In particular with reference to timber, the modulus of elasticity is representative of the quality of the wooden board and may be used to sort the various types of timber or to evaluate the different mechanical properties of different boards made of the same timber, or even to reject boards whose properties are unsuitable for the intended use (in particular in the construction sector).

At present, there are various devices and method for proof loading wooden boards and for defining their modulus of elasticity. Moreover, the prior art devices may be used independently or, as is more often the case, they may be integrated in production lines in large plant.

A first type of prior art device (described for example in patent DE 44 35 975) comprises the combined use of an apparatus for X-ray scanning the boards and a device for evaluating the frequency response of the boards struck by a suitable percussion tool.

In contrast, in a second type of device for evaluating the modulus of elasticity, described in U.S. Pat. No. 3,714,820, a succession of boards is fed to a suitable test station. In this case, the boards are arranged with their main axis of extension perpendicular to the direction of feed.

Once they have arrived close to said station, the boards are picked up, one at a time, and opposite jaws grip the opposite ends of the boards to apply a tractive force and to elongate them.

A suitable sensor evaluates the value of the elongation produced and a microprocessor unit calculates the value of the modulus of elasticity as the ratio of the force applied to the board to the elongation induced. In that way a value of the overall modulus of elasticity for the entire wooden board is obtained.

However, said device has several disadvantages.

First, in said type of device, proof loading is carried out using a tensile test for each board and, consequently, the boards must be fed one at a time to the test station, stopping all of the others until the test is complete.

This causes overall slowing of the succession of boards and so a reduction in the speed with which proof loading is carried out, consequently reducing overall plant productivity.

In this context, the technical purpose of the present invention is to propose a device and a method for proof loading wooden boards which are free of the above-mentioned disadvantages.

In particular, the present invention has for an aim to propose a device and a method for proof loading wooden boards which allow the tensile test to be carried out rapidly and continuously (in particular without stopping board feed).

The present invention also has for an aim to propose a device and a method for proof loading wooden boards which allow high production speeds in plants.

Yet another aim of the present invention is to propose a device and a method for proof loading wooden boards which also allow their modulus of elasticity to be defined.

The present invention has for another aim to propose a device and a method for proof loading wooden boards which allow a more precise estimate of the long modulus of elasticity the boards.

The technical purpose specified and the aims indicated are substantially achieved by a device for proof loading wooden boards and a method for proof loading wooden boards as described in one or more of the claims herein.

Further characteristics and advantages of the present invention are more apparent from the description which follows of several preferred, non-limiting embodiments of a device and a method for proof loading wooden boards, illustrated in the accompanying drawings, in which:

FIG. 1 is a schematic side view of a first embodiment of a device for proof loading wooden boards according to the present invention;

FIGS. 1a and 1b show respective enlarged details of the device of FIG. 1;

FIG. 2 is a schematic side view of a second embodiment of a device for proof loading wooden boards according to the present invention;

FIGS. 2a and 2b show respective enlarged details of the device of FIG. 2;

FIG. 3 is a schematic side view of a third embodiment of a device for proof loading wooden boards according to the present invention;

FIGS. 3a and 3b show respective enlarged details of the device of FIG. 3.

With reference to the accompanying drawings the numeral 1 denotes as a whole a device for proof loading wooden boards 2 made in accordance with the present invention.

However, in particular, the accompanying drawings show the most complete case, in which the device for proof loading also allows definition of the modulus of elasticity of the wooden boards 2.

Therefore, hereinafter, the present invention will be described both with reference to the basic case for proof loading only, and with reference to the most complex case for definition of the modulus of elasticity (to define this the device must comprise additional characteristics compared with those for only proof loading with the tensile test).

In general, the device 1 comprises a supporting structure for the various parts (not illustrated in the accompanying drawings) on which there are mounted first feed means 3 and second feed means 4 respectively positioned at a first segment 5 and a second segment 6 of a feed path along which the boards 2 are fed parallel with their main direction of extension.

In the accompanying drawings, at the device 1, the feed path extends between an infeed station 7 and an ouffeed station 8 upstream and downstream of which there are suitable means M for moving the boards. The direction of feed is indicated by the arrow labelled D.

With reference to the direction of feed of the boards 2 along the feed path, the second segment 6 of the feed path is upstream of the first segment 5.

Moreover, the first and second feed means 3, 4 are arranged relative to each other in such a way that they can act simultaneously on two different portions of the same wooden board 2 which is being fed along the feed path.

The device 1 for proof loading boards 2 also comprises means 9 for deforming the boards 2, designed to cause the boards 2 to elongate along their main direction of extension.

If the device 1 is also intended to define the modulus of elasticity of the boards 2, it also comprises means 10 for detecting the elongation produced in the boards 2 by the deformation means 9, and processing and control means 11 operatively connected to the deformation means 9 and to the detector means 10 for defining the modulus of elasticity of the boards 2. In this case, the elongation induced in the boards 2 must be of the elastic type.

In accordance with the present invention, the deformation means 9 comprise the first and second feed means 3, 4 and through the gripping action which the latter develop on the boards 2, they can apply a longitudinal tractive force on the boards 2.

Advantageously, the first and second feed means 3, 4 are made in such a way that they guarantee a secure grip on the boards 2 without the risk of any slipping between them and the boards 2.

In the preferred embodiments the operating distance between the first and second feed means 3, 4 may be adjusted according to requirements.

To guarantee the secure grip of the first and second feed means 3, 4 on the boards 2, in the preferred embodiments the first feed means 3 comprise at least a first pulling element 12 and a second pulling element 13 positioned in such a way that they are facing and opposite each other which, in practice, can be connected by friction to two opposite faces 14 of the boards 2. Advantageously, the distance between the first and second pulling elements 12, 13 can be adjusted to suit the thickness of the boards 2 to be measured.

Whilst in other embodiments they may consist of one or more rollers, in those illustrated in the accompanying drawings the first and second pulling elements 12, 13 each consist of a conveyor belt.

Both in the case in which they consist of one or more rollers, and in the case illustrated, the first and second pulling elements 12, 13 rotate in opposite directions to each other in such a way that, at the zone facing the board 2, each has a speed in the same direction as that of the board 2.

Thus, in the embodiments illustrated, the first and second pulling elements 12, 13 respectively comprise two first pulling rollers 15 and two second pulling rollers 16 arranged with the axis of rotation perpendicular to the board 2 feed path and parallel with the surface of the boards 2 on which they act. Wound around the first and second rollers 15, 16 there are respectively a first and a second belt 17, 18 made of a material able to apply a high level of friction/grip to the surface of the wooden boards 2.

Similarly, in the preferred embodiments, the second feed means 4 comprise at least a third pulling element 19 and a fourth pulling element 20 positioned in such a way that they are facing and opposite each other which, in practice, can be connected by friction to two opposite faces 14 of the boards 2.

Advantageously, the distance between the third and fourth pulling elements 19, 20 can also be adjusted to suit the thickness of the boards 2 to be measured.

Whilst in other embodiments they may consist of one or more rollers, in those illustrated in the accompanying drawings the third and fourth pulling elements 19, 20 each consist of a conveyor belt. Both in the case in which they consist of one or more rollers, and in the case illustrated, the third and fourth pulling elements 19, 20 rotate in opposite directions to each other in such a way that, at the zone facing the board 2, each has a speed in the same direction as that of the board 2.

Thus, in the embodiments illustrated, the third and fourth pulling elements 19, 20 respectively comprise two third pulling rollers and two fourth pulling rollers 21, 22 arranged with the axis of rotation perpendicular to the board 2 feed path and parallel with the surface of the boards 2 on which they act. Wound around the third and fourth rollers 21, 22 there are respectively a third and a fourth belt 23, 24 made of a material able to apply a high level of friction/grip to the surface of the wooden boards 2.

In general, either the first or the second feed means 3, 4 are designed to feed the boards 2 forwards with a predetermined speed (advantageously constant), whilst the other feed means (respectively the second 4 or the first 3) are designed to apply a predetermined longitudinal tractive force on the boards 2 without having to stop board 2 feed along the movement path.

In particular, in the embodiment illustrated in FIG. 1, the second feed means 4 are designed to feed the boards 2 with a predetermined speed, preferably constant, whilst the first feed means 3 are designed to apply an accelerating force F on the portions of boards 2 located at them.

As regards the second feed means 4 (FIG. 1*a*), at least one of the third and the fourth pulling elements 19, 20, and advantageously both, is motor-driven and the speed of the motor is controlled directly by the processing and control means 11. If only one of the third and the fourth pulling elements 19, 20 is motor-driven, the other is preferably idle and acts as a contact element.

In contrast, as regards the first feed means 3 (FIG. 1*b*), again at least one of the first and second pulling elements 12, 13 (advantageously both) is motor-driven, but its speed is not controlled. In contrast, the torque supplied by the motor (not illustrated) connected to the first and/or the second pulling element 13 is controlled by the processing and control means 11.

Said torque is kept at a level such that it causes an elastic traction on the boards 2.

In the embodiment in FIG. 2, the situation is inverted compared with what is illustrated in FIG. 1. In FIG. 2 the first feed means 3 are designed to feed the boards 2 with a predetermined speed (advantageously constant), whilst the second feed means 4 are designed to apply a braking force on the boards 2 as they are fed along the feed path.

As regards the first feed means 3 (FIG. 2*b*), at least one of the first and the second pulling elements 12, 13, and advantageously both, is motor-driven and the speed of the motor (not illustrated) is controlled directly by the processing and control means 11. If only one of the first and the second pulling elements 12, 13 is motor-driven, the other is preferably idle and acts as a contact element.

In contrast, as regards the second feed means 4 (FIG. 2*a*), in this case at least one of the third and the fourth pulling elements 19, 20, or both, is braked with a torque controlled by the processing and control means 11. This may be achieved either with an electromagnetic brake or with any other method.

As regards the characteristics which allow the definition of the modulus of elasticity of the boards 2, it should be noticed that in both of the embodiments illustrated in FIGS. 1 and 2, the detector means 10 directly or indirectly define the speed of board 2 feed at the first and the second feed means 3, 4, and the processing and control means 11 define the elongation of the boards 2 based on the speeds of the boards 2 detected at the first and second feed means 3, 4.

In particular, the detector means 10 comprise a detector 25 which is operatively connected to the board 2 at the feed means which apply the tractive force (the first feed means 3 in Figure and the second feed means 4 in FIG. 2) to detect a value V1 of the board 2 speed in said zone.

For example, the detector 25 may be connected to one of the belts 17, 18, 23, 24 of the pulling elements 12, 13, 19, 20 to detect its speed or directly to the board 2. Alternatively, the detector 25 may be an encoder connected to one of the rollers 15, 16, 21, 22 of the pulling element 12, 13, 19, 20 involved.

The detector 25 sends to the processing and control means 11 a signal S1 representing the instantaneous speed of the board 2 at the feed means 2, 3 designed to apply the tractive force.

In turn, the processing and control means 11, which also know the value of the speed V2 of the board 2 at the feed means 3, 2 designed to feed it forward with a predetermined speed, can calculate the value of the elongation of each portion of the board 2 by time integration of the difference between the value V1 and the value V2 (described in more detail below). In the accompanying drawings S2 is used to label the signal exchanged by the processing and control means to keep the speed V2 at the predetermined value.

Indeed, the speed V1 varies, from one moment to the next, according to the portion of the board 2 which is located between the first and the second feed means 3, 4.

The value of said difference is then subjected, by the processing and control means 11, to a time integration operation to define the instantaneous value of the elongation.

The processing unit can then calculate the modulus of elasticity of the portion, considered from one moment to the next, of the board 2 as a ratio of the force "F" applied (known) to the value of the elongation produced and detected.

The processing and control means 11 can then supply the value of the overall modulus of elasticity of the entire board 2 using suitable calculation algorithms.

In other embodiments, of which an example is shown in FIG. 3, in contrast, the tractive force F on the boards 2 is transmitted to the boards 2 using the first and/or the second feed means 3, 4, on which one or more actuators act.

Therefore, in general, the first feed means 3 or the second feed means 4 have a fixed position relative to the feed path (that is to say, relative to the device 1 supporting structure) whilst, respectively, the second feed means 4 or the first feed means 3 can move relative to the supporting structure along the feed path. At least one actuator 26 is mounted between the supporting structure, to which the fixed feed means 2, 3 are secured, and the mobile feed means 3, 2 to apply the tractive force wanted on the boards 2.

In other, more complex embodiments, both the first and the second feed means 3, 4 may be able to move along the feed path and the actuator 26 may be mounted directly between the first and the second feed means 3, 4.

However, in all of these cases, both the first and the second feed means 3, 4 are designed to feed the boards 2 with equal predetermined speed V (preferably constant) according to the methods described above with reference to FIGS. 1 and 2.

In the embodiment in FIG. 3, the first feed means 3 (FIG. 3*b*) can move relative to the feed path, whilst the second feed means 4 (FIG. 3*a*) are fixed. Moreover, the actuator 26 applies on the first feed means 3 a force directed according to the direction of feed of the boards 2 along the feed path (accelerating force).

However, in other embodiments the actuator 26 may apply on the second feed means 4 a force directed in the opposite direction to the direction of feed of the boards 2 along the feed path (braking force).

In all of these embodiments (such as that of FIG. 3) the detector means 10 comprise a detector 25 acting on the actuator 26 to measure its extension.

In this configuration, the signal S1, acquired by the processing and control means 11, representing the extension of the actuator 26, from one moment to the next, directly represents the value of the elongation produced by the deformation of the board 2.

In this embodiment too, the processing and control means 11 then calculate the modulus of elasticity of the portion, considered from one moment to the next, of the board 2 as the ratio of the force "F" applied to the value of the elongation produced, as well as the overall modulus of elasticity using suitable calculation algorithms.

The method which also forms the subject matter of the present invention, implemented in the devices described above, comprises an operating feed step in which a wooden board 2 is fed along a feed path, and a traction step in which, between two different portions of the board 2, a tractive force is applied which acts along the main direction of extension of the board 2.

Moreover, in accordance with the present invention, on one hand, during the feed step, the board 2 is fed parallel with its own main direction of extension, and on the other hand, the traction step is carried out simultaneously with the feed step.

The tractive force is advantageously transmitted to the board 2 using a board 2 controlled feed step at its first portion, and a simultaneous conditioned feed step at its second portion.

In particular, the board 2 controlled feed step involves feeding the board 2 at a predetermined and/or constant speed, using feed means designed to impose the feed speed on the first portion of the board 2.

In contrast, in turn, the conditioned feed step involves the application of a longitudinal tractive force on the second portion of the board 2 while the latter passes at specific feed means.

In a first embodiment, the first portion of the board 2 where the controlled feed step is implemented, with reference to the feed path is upstream of the second portion where the conditioned feed step is implemented. In this case, the force applied on the board 2 during the conditioned feed step is in the same direction as the direction of board 2 feed.

In contrast, in a second embodiment, the first portion of the board 2 where the controlled feed step is implemented, with reference to the feed path is downstream of the second portion where the conditioned feed step is implemented. In this case, the force applied on the board 2 during the conditioned feed step is a braking force which acts in the opposite direction to the direction of board 2 feed.

When the method for proof loading also involves the possibility of defining the modulus of elasticity of the boards 2, it also involves two further operating steps: a step of detecting the elongation produced on the board 2 by the tractive force applied to it, and a step of calculating the modulus of elasticity of the board 2 based on the results of the step of detecting the elongation. Advantageously, said further two steps are also carried out simultaneously with the feed step.

As regards the step of detecting the elongation, depending on the embodiments, it may involve either direct detection of the elongation (for example by detecting the extension of one or more actuators, as in the embodiment illustrated in FIG. 3), or direct or indirect detection of the board 2 feed speed at each different portion.

In particular, if the first portion is subject to a predetermined feed speed V, detection of the speed is obviously indirect, since it is a value which is already preset and known to the processing and control means 11.

In contrast, as regards the second portion, the detecting step may involve either direct detection of the speed $V_2$ of the board 2, or detection of the speed of the feed means acting on the board 2.

Preferably, the detecting step involves calculation of board 2 elongation integral in the time of the difference between the speed of the portion of board 2 subject to controlled feed and the speed of the portion of board 2 subject to conditioned feed.

Advantageously, the method disclosed may be implemented repeatedly to allow the examination of a plurality of different segments, even partly overlapping, of the same board 2. In particular, it may be repeated in a practically continuous way for segments of the board 2 which are partly overlapping each other.

Since the board 2 is fed forwards continuously, it gradually presents to the first and the second feed means 3, 4 via new segments which can be examined.

Therefore, in the preferred embodiment, the method disclosed involves continuous examination of the entire board 2. In particular, in the embodiments which also involve definition of the modulus of elasticity, from one moment to the next all significant data (speed, elongation, force applied, etc.) is saved, which may then all be processed together to obtain all necessary information.

This is particularly useful if the tractive force is applied continuously on the board 2. In such a case, the elongation of each segment of the board 2 can only be calculated if the entire elongation is known from the time the force was initially applied on the board 2, because, from one moment to the next, what occurs is not an elongation of the segment of the board 2 subjected to the tractive force, but a variation in the elongation of said segment compared with the elongation of the segment examined the moment before.

Therefore, at the first moment of implementing the method, the board 2 being fed with a predetermined speed V, is subjected, between two of its portions, to a force F which causes an elongation X of the board 2, from which the modulus of elasticity E of said segment of the board 2 can be calculated.

However, keeping the force F constant, in the next moment (that is to say when a time $\Delta t$ has elapsed) the board 2 will be fed forwards by a segment $\Delta L$ and therefore the segment which will be examined will be partly or completely different compared with the previous one and will have its own modulus of elasticity $E \pm \Delta E$. Consequently, the elongation produced by the force F will be varied compared with that previously detected and will be equal to $X \pm \Delta X$. However, if the detector means 10 are designed to detect the speed of the elongated board 2 rather than directly detecting the elongation, what can be measured is only the variation in the elongation $\Delta X$.

The actual elongation, from which the modulus of elasticity can be calculated, may instead be calculated only based on the elongation X value previously detected.

This is then repeated for each segment of the board 2 which is examined after the others.

The present invention brings important advantages.

First, the present invention guarantees high plant productivity because board feed does not have to be stopped in order to perform proof loading and the modulus of elasticity is also defined if required.

Consequently, when the device is integrated in the production lines of a plant, the processing speed can be increased because the device does not require the boards to be stopped and plant productivity is therefore significantly increased.

The most complete embodiments of the device and the method described above allow a more precise evaluation of the modulus of elasticity. They allow simple, rapid definition of the modulus of elasticity not only of the entire board but also of a plurality of its segments.

It is therefore also possible to identify individual portions of the board which are characterised by a modulus of elasticity which is unsuitable for the intended use of the board.

It should also be noticed that the present invention is relatively easy to produce and that even the cost linked to implementing the invention is not very high.

The invention described may be modified and adapted in several ways without thereby departing from the scope of the inventive concept.

Moreover, all details of the invention may be substituted with other technical equivalent elements and in practice all of the materials used, as well as the shapes and dimensions of the various components, may be any according to requirements.

The invention claimed is:

1. A device for proof loading wooden boards, comprising: (a) first feed means (3) located at a first segment (5) of a feed path along which each of the boards (2) is fed in a direction parallel with each board's main direction of extension, and (b) second feed means (4) positioned at a second segment (6) of the feed path which, with reference to the direction of feed of the boards (2), is upstream of the first segment (5), the first and the second feed means (3), (4) being positioned relative to each other so they can simultaneously act on two different portions of the same wooden board (2) which is being fed along the feed path, the device comprising deformation means (9) effective to cause each board (2) to elongate, without bending, in a direction substantially parallel with its main direction of extension, the deformation means (9) comprising the first feed means (3) and the second feed means (4), the deformation means (9) being effective to apply a longitudinal tractive force on each board (2) using the first and the second feed means (3), (4), the longitudinal tractive force being applied in a direction substantially parallel with the board's main direction of extension and being effective to cause the board (2) to elongate, without bending, in a direction substantially parallel with the board's main direction of extension.

2. The device according to claim 1, wherein the first or respectively the second feed means are designed to feed the boards (2) forwards with a predetermined speed, and the second or respectively the first feed means are designed to apply a predetermined longitudinal tractive force on the boards (2) without stopping board (2) feed along the movement path.

3. The device according to claim 2, wherein the first feed means (3) are designed to feed the boards (2) forwards with a predetermined speed, and the second feed means (4) are designed to apply a braking force on the boards (2) as they are fed forwards along the feed path, or respectively the second feed means (4) are designed to feed the boards (2) forwards with a predetermined speed, and the first feed means (3) are designed to apply an accelerating force on the portions of boards (2) at the first feed means (3).

4. The device according to claim 3, characterised in that the first feed means (3) or respectively the second feed means (4) are designed to feed the boards (2) forwards at them with a constant speed.

5. The device according to claim 1, characterised in that the first feed means (3) or respectively the second feed means (4) have a fixed position relative to the feed path, also being characterised in that the second feed means (4) or respectively the first feed means (3) can move along the feed path, and in that the device also comprises at least one actuator (26) connected to the mobile feed means (4), (3) for applying said tractive force on the boards (2).

6. The device according to claim 5, wherein the first feed means (3) are designed to feed the boards (2) forwards with a predetermined speed, and the actuator (26) applies on the second feed means (4) a force directed in the opposite direction to the direction of feed of the boards (2) along the feed path, or respectively the second feed means (4) are designed to feed the boards (2) forwards with a predetermined speed, and the actuator (26) applies on the first feed means (3) a force directed in the same direction as the direction of feed of the boards (2) along the feed path.

7. The device according to claim 1, characterised in that the board deformation means (9) are designed to cause an elastic elongation of the boards (2), and also being characterised in that the device comprises:
   means (10) for detecting the elongation produced in the boards (2) by the deformation means (9); and
   processing and control means (11) operatively connected to the deformation means (9) and to the detector means (10) for defining the modulus of elasticity of the boards (2).

8. The device according to claim 3, characterised in that the board deformation means (9) are designed to cause an elastic elongation of the boards (2); in that the device comprises:
   means (10) for detecting the elongation produced in the boards (2) by the deformation means (9); and
   processing and control means (11) operatively connected to the deformation means (9) and to the detector means (10) for defining the modulus of elasticity of the boards (2);
in that the detector means (10) directly or indirectly define the feed speed of the boards (2) at the first and the second feed means (3), (4), and also in that the elongation of the boards (2) is defined based on the speed of the boards (2) detected at the first and the second feed means (3), (4).

9. The device according to claim 5, characterised in that the board deformation means (9) are designed to cause an elastic elongation of the boards (2); in that the device comprises:
   means (10) for detecting the elongation produced in the boards (2) by the deformation means (9); and
   processing and control means (11) operatively connected to the deformation means (9) and to the detector means (10) for defining the modulus of elasticity of the boards (2);
and in that the detector means (10) define the variation of the distance between the first feed means (3) and the second feed means (4).

10. The device according to claim 1, characterised in that the first feed means (3) comprise at least a first and a second pulling element (12), (13) which are positioned so that they are facing and opposite each other and, in practice, they can be connected by friction to two opposite faces (14) of the boards (2).

11. The device according to claim 10, wherein the pulling elements each comprise a roller or a conveyor belt (17), (18) rotating in opposite directions.

12. The device according to claim 1, characterised in that the second feed means (4) comprise at least a third and a fourth pulling element (19), (20) which are positioned so that they are facing and opposite each other and, in practice, they can be connected by friction to two opposite faces (14) of the boards (2).

13. The device according to claim 12, wherein the pulling elements each comprise a roller or a conveyor belt (23), (24) rotating in opposite directions.

14. A method for proof loading wooden boards, comprising:
   a feed operating step in which a wooden board (2) is fed forwards along a feed path;
   a traction step in which, between two different portions of the board (2), a tractive force is applied which extends along the main direction of extension of the board (2) to elongate, without bending, the board;
the method being characterised in that during the board (2) feed step it is fed forwards parallel with a main direction of extension of the board (2), and also being characterised in that the traction step is carried out simultaneously with the feed step.

15. The method according to claim 14, characterised in that the tractive force is transmitted to the board (2) by means of a board (2) controlled feed step at one of the different portions and a simultaneous conditioned feed step at the other portion.

16. The method according to claim 15, characterised in that the controlled feed step involves feeding the board (2) at a predetermined and/or constant speed.

17. The method according to claim 16, characterised in that the conditioned feed step involves the application of a tractive force in the same direction as the direction of feed of the board (2), at one of the different portions of the board (2) which is downstream of the other portion with reference to the direction of feed of the board (2), or respectively the application of a braking force in the opposite direction to the direction of feed of the board (2), at one of the different portions of the board (2) which is upstream of the other portion with reference to the direction of feed of the board (2).

18. The method according to claim 14, characterised in that it also comprises:
   a step of detecting the elongation produced on the board (2) by the tractive force applied to it; and
   a step of calculating the modulus of elasticity of the board (2) based on the results of the detecting step;
   said detecting and calculating steps being carried out simultaneously with the feed step.

19. The method according to claim 14, characterised in that the detecting step involves direct or indirect detection of the board (2) feed speed at each different portion.

20. The method according to claim 14, characterised in that said operating steps are carried out one after another for a plurality of different and/or partly overlapping segments of the same board (2).

* * * * *

UNITED STATES PATENT AND TRADEMARK OFFICE
CERTIFICATE OF CORRECTION

| | | |
|---|---|---|
| PATENT NO. | : 8,413,522 B2 | Page 1 of 1 |
| APPLICATION NO. | : 12/988601 | |
| DATED | : April 9, 2013 | |
| INVENTOR(S) | : Federico Giudiceandrea | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 316 days.

Signed and Sealed this
Thirteenth Day of August, 2013

Teresa Stanek Rea
*Acting Director of the United States Patent and Trademark Office*